US010265695B2

(12) United States Patent
Katano et al.

(10) Patent No.: US 10,265,695 B2
(45) Date of Patent: Apr. 23, 2019

(54) PIPETTING SYSTEM

(71) Applicant: ICOMES LAB Co., Ltd., Iwate (JP)

(72) Inventors: Keiji Katano, Iwate (JP); Tadataka Kamiyama, Iwate (JP)

(73) Assignee: ICOMES LAB CO., LTD., Iwate (JP)

( * ) Notice: Subject to any disclaimer, the term of this patent is extended or adjusted under 35 U.S.C. 154(b) by 129 days.

(21) Appl. No.: 15/459,395

(22) Filed: Mar. 15, 2017

(65) Prior Publication Data

US 2017/0274372 A1  Sep. 28, 2017

(30) Foreign Application Priority Data

Mar. 22, 2016 (JP) .................. 2016-056734

(51) Int. Cl.
  *B01L 3/02* (2006.01)
  *G01N 35/10* (2006.01)
  *B01L 99/00* (2010.01)

(52) U.S. Cl.
  CPC ........... *B01L 3/0217* (2013.01); *B01L 3/0237* (2013.01); *B01L 99/00* (2013.01); *G01N 35/1002* (2013.01); *G01N 35/1011* (2013.01); *G01N 35/1016* (2013.01); *B01L 3/0234* (2013.01); *G01N 2035/1013* (2013.01)

(58) Field of Classification Search
  CPC combination set(s) only.
  See application file for complete search history.

(56) References Cited

U.S. PATENT DOCUMENTS

| 4,671,123 A | * | 6/1987 | Magnussen, Jr. | ..... B01L 3/0227 |
| | | | | 422/926 |
| 4,821,586 A | * | 4/1989 | Scordato | ............... B01L 3/0227 |
| | | | | 422/926 |
| 5,343,769 A | * | 9/1994 | Suovaniemi | .......... B01L 3/0227 |
| | | | | 422/926 |

(Continued)

FOREIGN PATENT DOCUMENTS

| JP | 4654197 B2 | 3/2011 |
| JP | 2013-544634 A | 12/2013 |

OTHER PUBLICATIONS

Extended European Search Report issued in corresponding European Patent Application No. 17161051.2, dated Jun. 2, 2017.

*Primary Examiner* — Brian R Gordon
(74) *Attorney, Agent, or Firm* — McDermott Will & Emery LLP

(57) ABSTRACT

A pipetting system includes: a pipetting device; a pipetting container including a plurality of pipetting positions into each of which the pipetting device pipettes liquid; and a positional relation detector configured to detect a positional relation between a front-end position of a tip and each of the pipetting positions. The pipetting device includes circuitry configured to, when a pipetting switch that orders pipetting is turned on, on condition that the front-end position of the tip detected by the positional relation detector is located at one of pipetting positions that is indicated by a pipetting pattern set up in advance, allow pipetting corresponding to the pipetting pattern, and on condition that the front-end position of the tip detected by the positional relation detector does not correspond to a corresponding one of pipetting positions that is indicated by the pipetting pattern set up in advance, disallow the pipetting.

5 Claims, 7 Drawing Sheets

(56) References Cited

U.S. PATENT DOCUMENTS

| | | | |
|---|---|---|---|
| 6,254,832 B1* | 7/2001 | Rainin | B01L 3/0227 422/518 |
| 6,299,841 B1* | 10/2001 | Rainin | B01L 3/0227 422/518 |
| 7,976,793 B2 | 7/2011 | Solotareff et al. | |
| 9,156,031 B2 | 10/2015 | Gruner et al. | |
| 2008/0271514 A1 | 11/2008 | Viot et al. | |
| 2009/0049933 A1 | 2/2009 | Decaux et al. | |
| 2009/0074622 A1* | 3/2009 | Kalamakis | B01L 3/0217 422/400 |
| 2009/0117009 A1* | 5/2009 | Cote | B01L 3/0227 422/400 |
| 2009/0216465 A1* | 8/2009 | Millet | B01L 3/0217 702/50 |
| 2009/0274587 A1* | 11/2009 | Butz | B01L 3/0217 422/400 |
| 2010/0199788 A1* | 8/2010 | Ayliffe | B01L 3/0275 73/864.11 |
| 2010/0226825 A1* | 9/2010 | Beckey | B01L 3/0217 422/509 |
| 2011/0160909 A1 | 6/2011 | Glauser et al. | |
| 2012/0046883 A1* | 2/2012 | Ayliffe | B01L 3/021 702/26 |
| 2013/0078733 A1* | 3/2013 | Holmes | B01L 3/0217 436/174 |
| 2013/0267038 A1* | 10/2013 | Andersin | B01L 3/021 436/180 |
| 2013/0280143 A1* | 10/2013 | Zucchelli | B25J 9/1697 422/501 |
| 2014/0130614 A1 | 5/2014 | Zeng | |
| 2015/0000429 A1* | 1/2015 | Lind | B01L 3/0286 73/864.13 |
| 2016/0236189 A1* | 8/2016 | Izumo | B01L 3/021 |
| 2016/0310937 A1* | 10/2016 | Lind | B01L 3/0227 |
| 2017/0120235 A1* | 5/2017 | Miettinen | B01L 3/0217 |
| 2017/0173576 A1* | 6/2017 | Natsume | B01L 3/0237 |

* cited by examiner

| Pipette no.: No.1 | Experiment date: 2015/10/17 |
|---|---|
| Name of reagent: ○○○○ | Capacity: 20 μL |
| Name of worker: ×× ×× | Name of tip: ICL 20 μL–capacity tip |
| Temperature: 20°C | Humidity: 50% |
| Remarks: | |

| order | in/out | [Y] | [X] | Volume | Mixing | Speed | Time |
|---|---|---|---|---|---|---|---|
| 1 | in | - | - | 2.2 | 0.0 | Hi | 18: 01: 24 |
| 2 | out | A | 1 | 2.2 | 0.0 | Hi | 18: 01: 29 |
| 3 | in | - | - | 2.0 | 0.0 | Hi | 18: 01: 30 |
| 4 | out | A | 2 | 2.0 | 0.0 | Hi | 18: 01: 35 |
| 5 | in | - | - | 2.4 | 0.0 | Hi | 18: 01: 37 |
| 6 | out | A | 3 | 2.4 | 0.0 | Hi | 18: 01: 42 |
| 7 | in | - | - | 2.5 | 0.0 | Hi | 18: 03: 51 |
| 8 | out | B | 4 | 2.5 | 0.0 | Hi | 18: 05: 33 |
| 9 | in | - | - | 2.6 | 0.0 | Hi | 18: 05: 37 |
| 10 | out | B | 5 | 2.6 | 0.0 | Hi | 18: 05: 42 |
| 11 | in | - | - | 2.7 | 0.0 | Hi | 18: 05: 44 |
| 12 | out | B | 6 | 2.7 | 0.0 | Hi | 18: 05: 49 |
| 13 | in | - | - | 2.8 | 0.0 | Hi | 18: 05: 51 |
| 14 | out | C | 1 | 2.8 | 0.0 | Hi | 18: 05: 58 |
| 15 | in | - | - | 2.9 | 0.0 | Hi | 18: 06: 00 |
| 16 | out | C | 2 | 2.9 | 0.0 | Hi | 18: 06: 05 |
| 17 | in | - | - | 3.0 | 0.0 | Hi | 18: 06: 06 |
| 18 | out | C | 3 | 3.0 | 0.0 | Hi | 18: 06: 13 |
| 19 | in | - | - | 3.1 | 0.0 | Hi | 18: 06: 15 |
| 20 | out | D | 4 | 3.1 | 0.0 | Hi | 18: 06: 21 |
| 21 | in | - | - | 3.2 | 0.0 | Hi | 18: 06: 23 |
| 22 | out | D | 5 | 3.2 | 0.0 | Hi | 18: 06: 29 |

PIPETTING SYSTEM

CROSS-REFERENCE TO RELATED APPLICATION(S)

The present application claims priority to and incorporates by reference the entire contents of Japanese Patent Application No. 2016-056734 filed in Japan on Mar. 22, 2016.

BACKGROUND

1. Technical Field

The disclosure relates to a pipetting system.

2. Related Art

One conventionally known pipetting device drives a motor to rotate an output shaft about the shaft center of the output shaft, thereby putting a piston into reciprocating motion in the axial direction of the piston inside a syringe to aspire and discharge liquid such as reagent or specimen through a nozzle at the front end of the pipetting devices.

Pipetting devices are typically manually operated and, for example, each performs pipetting, with the housing thereof gripped with the palm and the fingers other than the thumb of a hand, in response to a push operation performed with the thumb on a knob (switch) provided on the base-end side (rear-end side) of the pipetting device. For example, Japanese Patent No. 4654197 and Published Japanese Translation of PCT International Publication No. 2013-544634 disclose pipetting devices each configured to be operated, while being held with the housing thereof gripped by the palm and the fingers other than the thumb of a hand, with a knob for aspiration and dispensing pushed by the thumb.

Each of the pipetting devices disclosed in Japanese Patent No. 4654197 and Published Japanese Translation of PCT International Publication No. 2013-544634 includes a wireless communication unit capable of wirelessly communicating with an external device. A pipetting system includes: the pipetting device including this wireless communication unit; and an external device capable of wireless communication.

Conventionally, even a pipetting device that is capable of accurately pipetting liquid, such as reagent, into small wells in a microplate (of 96 wells or 384 wells, for example) has not been able to determine whether a position of a well into which the reagent has been pipetted is a position into which the liquid should be pipetted. Incorrect positioning highly likely occurs in pipetting particularly not only because pipetting work needs to follow a pipetting pattern defined in accordance with a sequence for pipetting, pipetting positions, pipetting volumes, and the like but also because the pipetting positions are small.

In view of the foregoing circumstances, it is desirable to provide a pipetting system capable of preventing incorrectly positioned pipetting.

SUMMARY

According to one aspect of the disclosure, there is provided a pipetting system including: a pipetting device including: a rotation actuator; a piston; a syringe in which the piston is reciprocated in an axial direction of the piston when the rotation actuator is driven; and a tip attached to a nozzle at a front end of the pipetting device, the pipetting device being configured to, upon being switched on, aspirate or dispense liquid through the tip; a pipetting container including a plurality of pipetting positions into each of which the pipetting device pipettes liquid; and a positional relation detector configured to detect a positional relation between a front-end position of the tip and each of the pipetting positions. The pipetting device includes circuitry configured to, when a pipetting switch that orders pipetting is turned on, on condition that the front-end position of the tip detected by the positional relation detector is located at one of pipetting positions that is indicated by a pipetting pattern set up in advance, allow pipetting corresponding to the pipetting pattern, and on condition that the front-end position of the tip detected by the positional relation detector does not correspond to a corresponding one of pipetting positions that is indicated by the pipetting pattern set up in advance, disallow the pipetting.

The above and other objects, features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 5 is a view depicting an example of how a pipetting pattern is displayed on a display screen;

FIG. 7 is a view depicting an example of a pipetting log.

DETAILED DESCRIPTION

The following describes an embodiment for carrying out this disclosure with reference to the accompanying drawings.

Configuration of Pipetting Device

Figure 1:
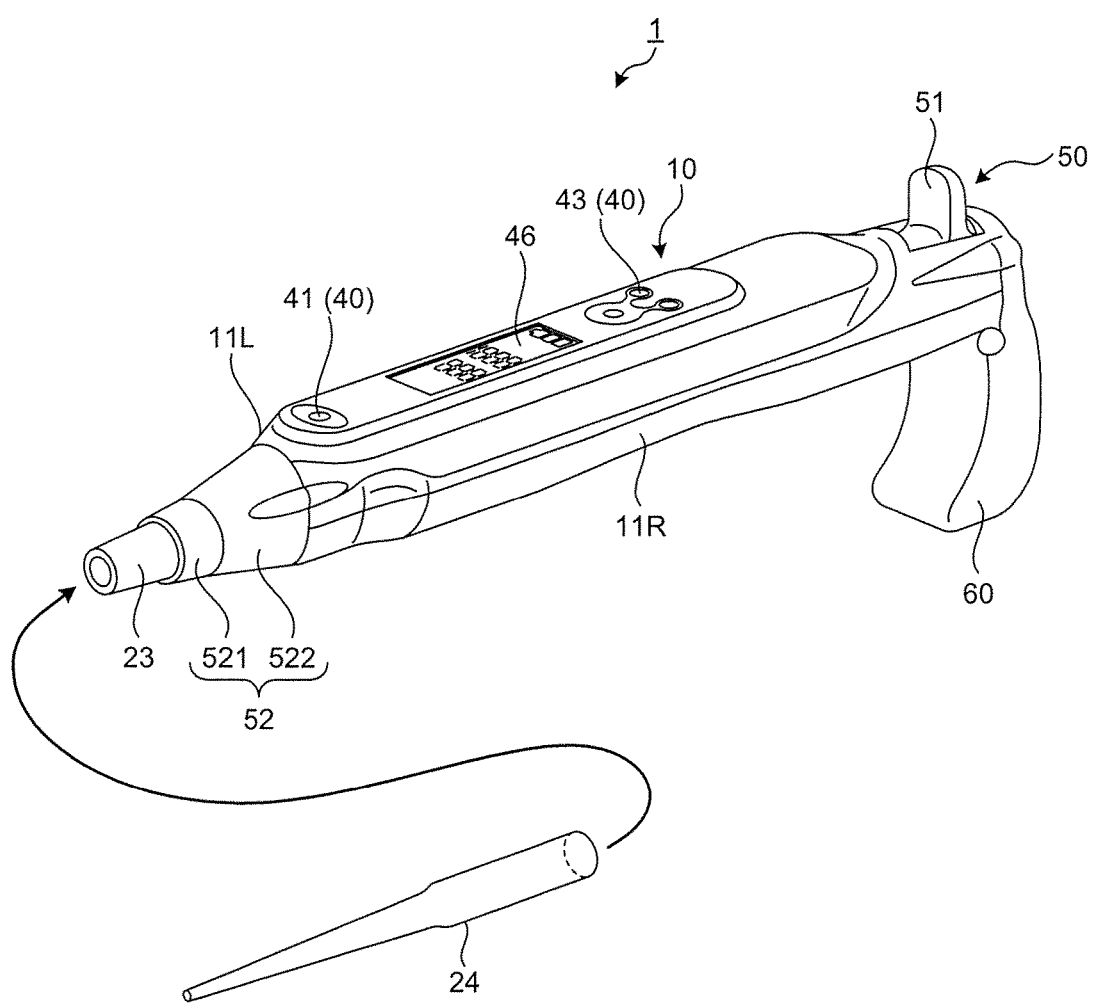
FIG. 1 is a perspective view of a pipetting device, viewed from the front-end side thereof, included in a pipetting system constituting an embodiment of the disclosure.

FIG. 1 is a perspective view of a pipetting device 1, viewed from the front-end side thereof, included in a pipetting system constituting an embodiment of the disclosure. The pipetting device 1 illustrated here is configured to aspirate and dispense liquid such as reagent or specimen, and includes a device body 10. The device body 10 is a housing having an accommodating space formed inside with a pair of left and right side covers 11L and 11R joined to each other. Each of these side covers 11L and 11R longitudinally extends from the front to the rear, so that the full length of the device body 10 is larger than the full width thereof.

The pipetting device 1 includes a finger rest section 60 at the base-end side of the device body 10. The finger rest section 60 extends in a direction intersecting the longitudinal direction of the device body 10 and has an accommodating space formed inside. In this embodiment, the front-end side of the finger rest section 60 curves toward the front-end side of the pipetting device 1.

Figure 2:
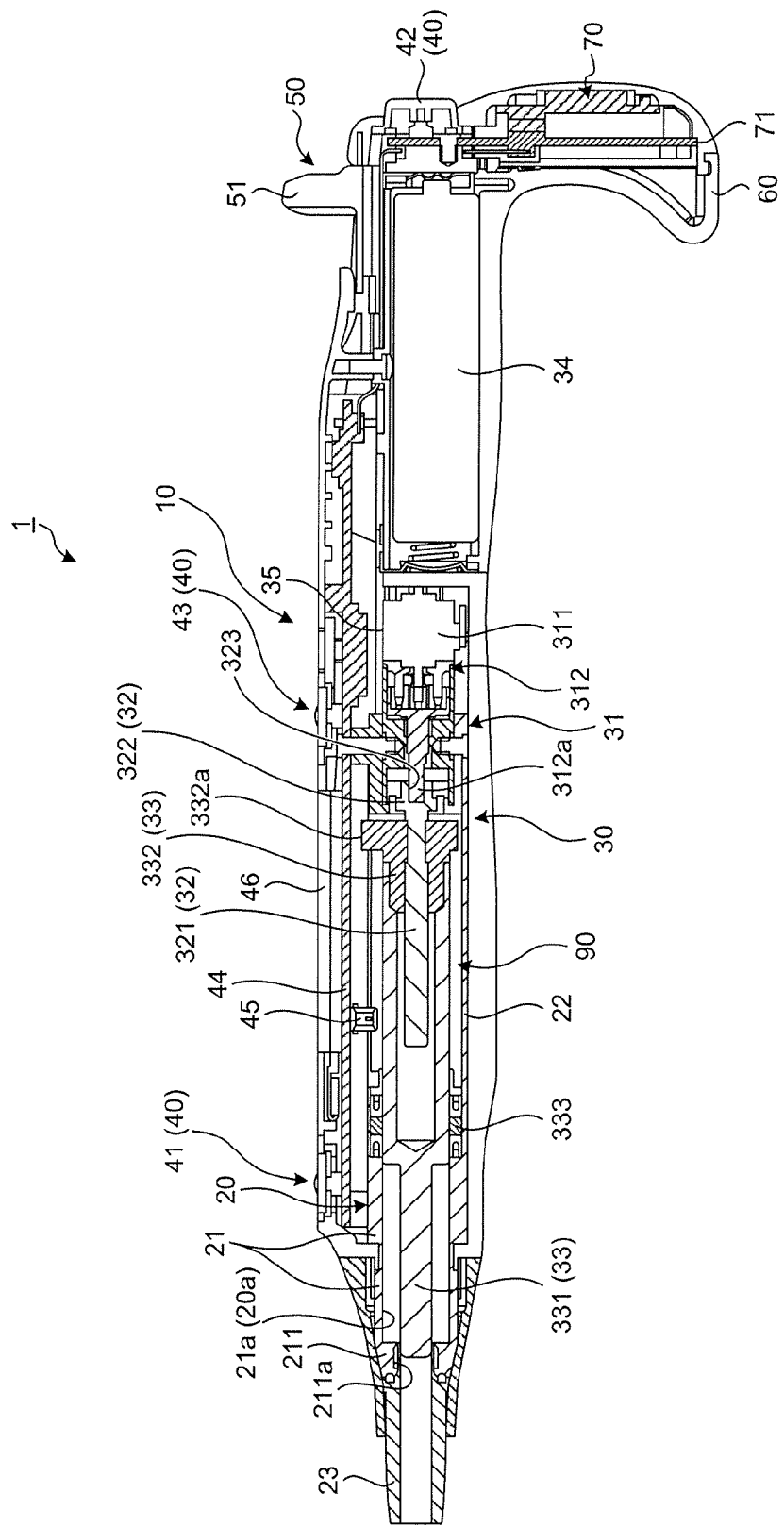
FIG. 2 is a schematic illustration depicting a vertical cross-section of the pipetting device included in the pipetting system constituting the embodiment of the disclosure.

FIG. 2 is a schematic illustration depicting a vertical cross-section of the pipetting device 1 included in the pipetting system constituting the embodiment of the disclosure. Inside the device body 10 and the finger rest section 60, a pipetting mechanism 90, an operation input unit (an operation input section or an input interface) 40, an ejection mechanism 50, and a wireless communication unit 70 are provided. The pipetting mechanism 90 includes a syringe 20 and an actuator unit 30.

The syringe 20 includes a syringe front-end section 21 and a syringe base-end section 22, and there is a syringe hollow part 20a formed between the syringe 20 and a piston 33. The syringe front-end section 21 has a columnar front-end hollow part 21a inside, and a front-end region 211 of the front-end hollow part 21a has a tapered shape the outer diameter of which decreases as approaching the front end of the front-end region 211.

A circular attachment aperture 211a is formed in the front end face of the syringe front-end section 21, the circular attachment aperture 211a communicating with the front-end hollow part 21a. On the front end face of the syringe front-end section 21, a nozzle 23 is attached in a manner that allows blockage of the attachment aperture 211a.

The syringe front-end section 21 is attached to the side covers 11L and 11R, so that the syringe 20 is disposed so as to block a front-end side aperture of the device body 10 when the syringe base-end section 22 has been inserted in the accommodating space inside the device body 10. The front end region 211 of the syringe front-end section 21 is exposed to the outside of the device body 10.

The actuator unit 30 includes a rotation actuator 31, an output shaft 32, and a piston 33. The rotation actuator 31 includes an electric motor 311 and a speed reducer 312. The electric motor 311 functions as a driving source of the rotation actuator 31, and enables the driving by using electric power and instructions. The electric power is supplied from, for example, a battery 34 accommodated in the base-end side of the accommodating space of the device body 10. The instructions are provided from a control circuit unit 80 described later. The electric motor 311 is a motor the rotational direction of which can be changed as desired in accordance with the direction of electrical conduction.

An actuator case 35 has a substantially cylindrical form, and extends over a length sufficient to cover the outer circumferential region of a driving shaft section 312a that constitutes a front end section of a speed reducer 312. This actuator case 35 covers an outer circumferential part of the speed reducer 312 in a manner such that the central axis of the actuator case 35 and the central axis of the driving shaft section 312a extend along the same line.

The output shaft 32 includes: a columnar output base section 321 having a screw groove in the outer circumferential surface thereof; and an output base-end section 322 provided in a form continuing from the base-end side of the output base section 321. The output base-end section 322 is diametrically larger than the output base section 321, and has a part thereof formed into an output concave part 323 by being biforked in a manner such that opposed surfaces constitute flat surfaces.

The piston 33 includes a piston body 331 and a nut 332. The piston body 331 has the front end thereof blocked and has a substantially cylindrical shape, and the outer diameter of the piston body 331 is slightly smaller than the inner diameter of the front-end hollow part 21a that constitutes the syringe hollow part 20a. A seal 333 made of an elastic body material is wound around the outer circumferential part of the front-end side of the piston body 331. The inner diameter of the piston body 331 is slightly larger than the outer diameter of the output shaft 32, that is, the outer diameter of the output base section 321 of the output shaft 32. The outer diameter of the front-end side of the piston body 331 is slightly smaller than the inner diameters of the attachment aperture 211a of the syringe 20 and the nozzle 23. The piston 33 is constantly biased toward the base-end side thereof by a biasing device such as a spring (not illustrated).

The nut 332 is attached to a base-end section of the piston body 331 and is made of, for example, a resin material. The nut 332 has a screw groove formed in the inner circumferential surface thereof and is disposed on the output shaft 32 with the screw groove thereof engaged with the screw groove of the output shaft 32. The nut 332 had a protruding piece 332a extending diametrically outward formed on the outer circumferential part.

The operation input unit 40 is provided for a worker (user) to input operations, and includes a first push button (front-end side push button) 41, a second push button (base-end side push button) 42, and an operation button 43.

The first push button 41 is provided at a location in the device body 10 that is close to the front-end side thereof, and a top part of the first push button 41 is exposed from the device body 10. When a push operation is performed thereon, this first push button 41 turns on a switch attached to a surface (the upper surface in FIG. 2) on one side of the control circuit board 44. In this embodiment, one of the surfaces of the control circuit board 44 on one side on which the first push button 41 is disposed is referred to as one surface (the upper surface), and the other one opposite to the surface on the side on which the first push button 41 is disposed is referred to as the other surface (a lower surface). The control circuit board 44 is accommodated in the accommodating space of the device body 10, and has the control circuit unit 80 (not illustrated in FIG. 2) described later mounted thereon that controls operation of the pipetting device 1.

The second push button 42 is provided on the base-end section of the device body 10, and a top part of the second push button 42 is exposed from the device body 10. When a push operation is performed thereon, this second push button 42 turns on an embedded switch and provides the control circuit unit 80 with a signal indicating the turning on.

The operation button 43 is provided at a location that is closer to the base-end side than the first push button 41 is, and a top part of the operation button 43 is exposed from the upper surface of the device body 10. This operation button 43 includes a plurality of push buttons. When a push operation is performed on any one of these push buttons is pushed, this operation button 43 provides, to the control circuit unit 80, an input instruction assigned to each of the push button. Between this operation button 43 and the first push button 41, a display section 46 constructed of, for example, a liquid crystal display (LCD) is provided in the upper surface of the device body 10. This display section 46 displays various kinds of information based on instructions provided by the control circuit unit 80. An informing section 47 described later is further provided next to the display section 46.

The ejection mechanism 50 includes an ejection lever 51 and an ejector 52. The ejector 52 includes: a cylindrical section 521 the inner diameter of which is larger than the nozzle 23; and a tapered section 522 that is provided as a section continuing from the base-end portion of this cylindrical section 521 and has the outer diameter and the inner diameter increasing as approaching the base end. A tip 24 such as a pipette tip is detachably attached to the nozzle 23.

The ejection lever 51 is provided in such a manner as to project to the outside beyond apertures on the base-end sides of the side covers 11L and 11R that constitute the device body 10. This ejection lever 51 is coupled to a base-end section of an ejection rod (not illustrated).

The wireless communication unit 70 is disposed in the base-end side of the pipetting device 1, that is, inside the finger rest section 60. The wireless communication unit 70 is provided on a communication circuit board 71 accommodated inside the finger rest section 60, as illustrated in FIG. 2.

The communication circuit board 71 is connected to the control circuit board 44 via, for example, a flexible printed circuit (FPC) connector and a flexible cable, and is capable of transmitting information received by the wireless communication unit 70 to the control circuit board 44. The communication circuit board 71 is also capable of transmitting information transmitted thereto by the control circuit board 44 to the wireless communication unit 70 via the FPC connector and the flexible cable.

In the initial state after the power-on of the pipetting device 1 configured in the above manner, the piston 33 of the actuator unit 30 is situated at a reference position, and the protruding piece 332a of the nut 332 is situated at a position in a detectable area of an origin detecting sensor 45, which is closer to the front-end side than the position where it is illustrated as being in FIG. 2.

In response to a push operation performed on the first push button 41 or the second push button 42 with the piston 33 thus situated at the reference position, the control circuit unit 80 controls the pipetting mechanism 90. Specifically, the control circuit unit 80 provides a driving instruction to the electric motor 311, thereby driving the electric motor 311. Here, a time period for which the control circuit unit 80 drives the electric motor 311 is a time period sufficient for aspirating a volume that has been set up in advance by being input through, for example, the operation button 43.

With the electric motor 311 thus driven, the output shaft 32 rotates about the shaft center thereof. With the output shaft 32 rotating relative to the actuator case 35, the piston 33 including the nut 332 engaged with the output shaft 32 linearly moves toward the base-end side in a direction along the shaft center of the output shaft 32 while being acted upon by the biasing force of the biasing device. With the piston 33 linearly moving toward the base-end side, the syringe hollow part 20a of the syringe 20 comes under negative pressure, so that liquid such as liquid reagent is aspirated into the tip attached to the nozzle 23.

When the control circuit unit 80 stops driving the electric motor 311, the piston 33 is situated at an advanced position at which the piston 33 is nearest possible to the base-end side. As a result of a push operation performed on the operation button 43 with the piston 33 having been moved to the advanced position, the pipetting device 1 is set to a dispending mode.

In response to a push operation performed on the first push button 41 or the second push button 42 with the pipetting device 1 thus having been set to the dispending mode, the control circuit unit 80 provides a driving instruction to the electric motor 311, thereby driving the electric motor 311. Under the dispending mode, the direction of electrical conduction is set so that the rotational axis of the electric motor 311 can be rotated in a direction opposite to a direction in which it is rotated for the aspiration. A time period for which the control circuit unit 80 drives the electric motor 311 is a time period sufficient for dispensing a volume that has been set in advance by being input through, for example, the operation button 43, which is a time period that allows the set amount to be dispensed each time one push operation is performed on the first push button 41 or the second push button 42.

With the electric motor 311 driven in the foregoing manner, rotative force corresponding to appropriate speed reduction by the speed reducer 312 is transmitted to the output shaft 32, so that the output shaft 32 rotates about the shaft center thereof relative to the actuator case 35 (syringe 20). With the output shaft 32 rotating relative to the actuator case 35, the piston 33 including the nut 332 engaged with the output shaft 32 linearly moves by a certain distance toward the front-end side in a direction along the shaft center of the output shaft 32 while resisting the biasing force of the biasing device. As a result of the linear movement of the piston 33 toward the front-end side, a part (a certain amount) of the liquid aspirated into the tip is pipetted.

In the pipetting device 1, each time such a push operation is performed on the first push button 41 or the second push button 42, the piston 33 linearly moves by a certain distance toward the front-end side and a certain volume of liquid is dispensed. The protruding piece 332a of the nut 332 included in the piston 33 then comes to a position in the detectable area of the origin detecting sensor 45, and the piston 33 comes to the reference position. This dispending operation is thereby ended.

Next, operations for detaching the tip 24 attached to the nozzle 23 in the pipetting device 1 are described. When the ejection lever 51 is pressed toward the front-end side, the ejection lever 51 coupled by an ejection rod (not illustrated) moves toward the front-end side while resisting the biasing force of an ejection spring (not illustrated). Consequently, the ejector 52 coupled to the ejection lever 51 moves relative to the nozzle 23 and presses the tip attached to the nozzle 23, thereby enabling detachment of the tip from the nozzle 23.

Pipetting System

Figure 3:
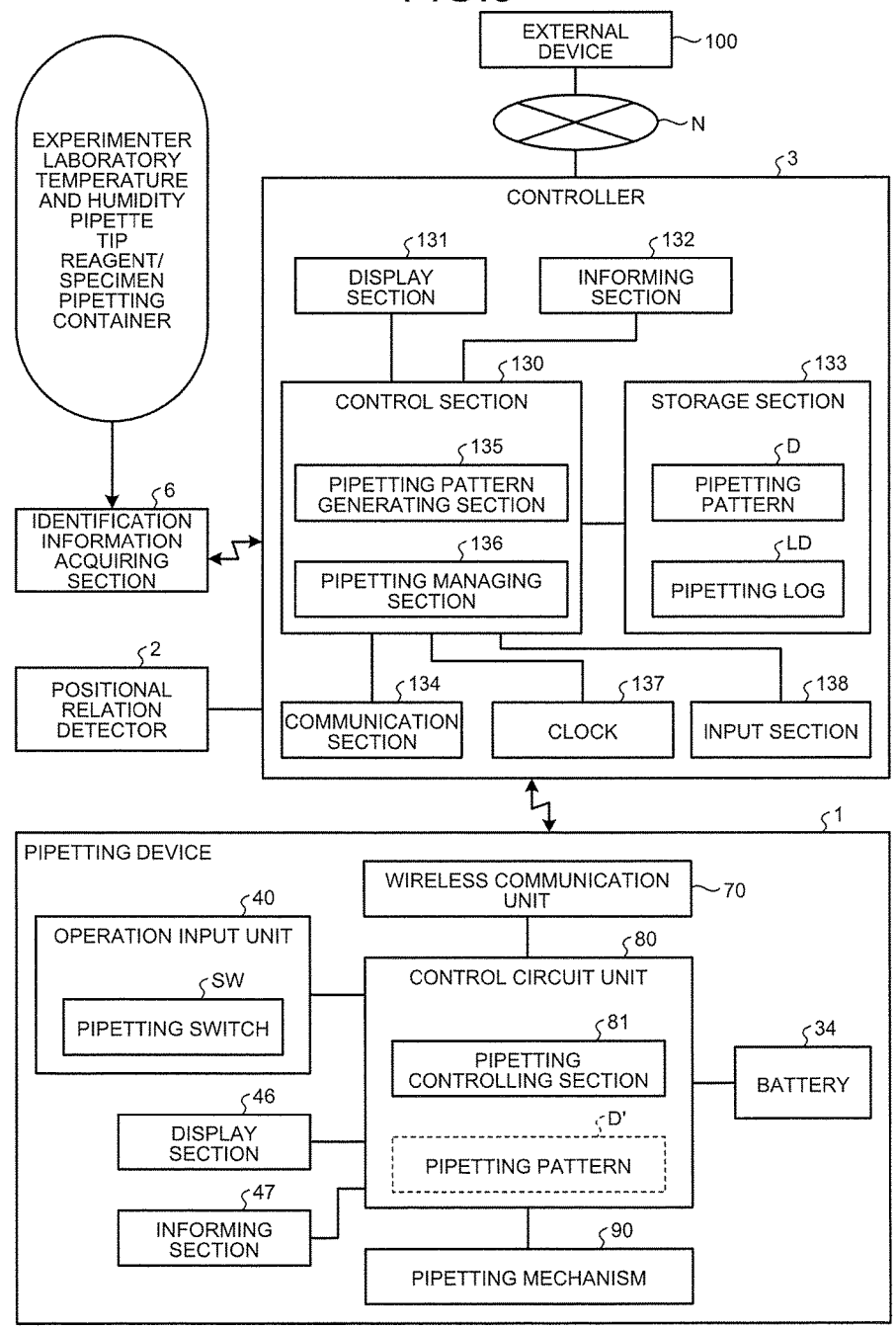
FIG. 3 is a block diagram depicting the configuration of the pipetting system constituting the embodiment of the disclosure.

FIG. 3 is a block diagram depicting the configuration of the pipetting system constituting the embodiment of the disclosure. In the pipetting system, the pipetting device 1, a positional relation detector 2, and an identification information acquiring section 6 are communicably connected to a controller 3 as illustrated in FIG. 3. The controller 3 is connected to an external device 100 through a network N.

The pipetting device 1 drives the rotation actuator 31 to cause the piston 33 to make a reciprocating motion inside the syringe 20 in the axial direction of the piston 33, and, upon being switched on with the first push button 41 or the like pushed, aspirates and dispenses liquid through the tip 24 attached to the nozzle 23 at the front end. In particular, the pipetting device 1 pipettes liquid into a well (a pipetting position) in a pipetting container such as a microplate.

In the pipetting device 1, the operation input unit 40, the display section 46, the informing section 47, the wireless communication unit 70, the pipetting mechanism 90, and the battery 34 are connected to the control circuit unit 80 as described above. The operation input unit 40 includes a pipetting switch SW that is turned on in response to pushing of the first push button 41. The control circuit unit 80 includes a pipetting controlling section 81.

Before the start of pipetting, a pipetting pattern D set up in advance is read out from the controller 3 into the control circuit unit 80 and stored therein as a pipetting pattern D'. When the pipetting switch SW that orders pipetting is turned on, if the front-end position of the tip 24 detected by the positional relation detector 2 is located at a pipetting position (a well) indicated by the pipetting pattern D' set up in advance, the pipetting controlling section 81 allows pipetting corresponding to the pipetting pattern D'. If the front-end position of the tip 24 detected by the positional relation detector 2 is not located at the pipetting position (the well) indicated by the pipetting pattern D' set up in advance, the pipetting controlling section 81 disallows the pipetting.

The positional relation detector 2 detects the positional relation between the front-end position of the tip 24 of the pipetting device 1 and a pipetting position such as a well, based on an image captured by an image capturing device such as a camera. The positional relation detector 2 is connected via USB connection, for example.

Figure 4:
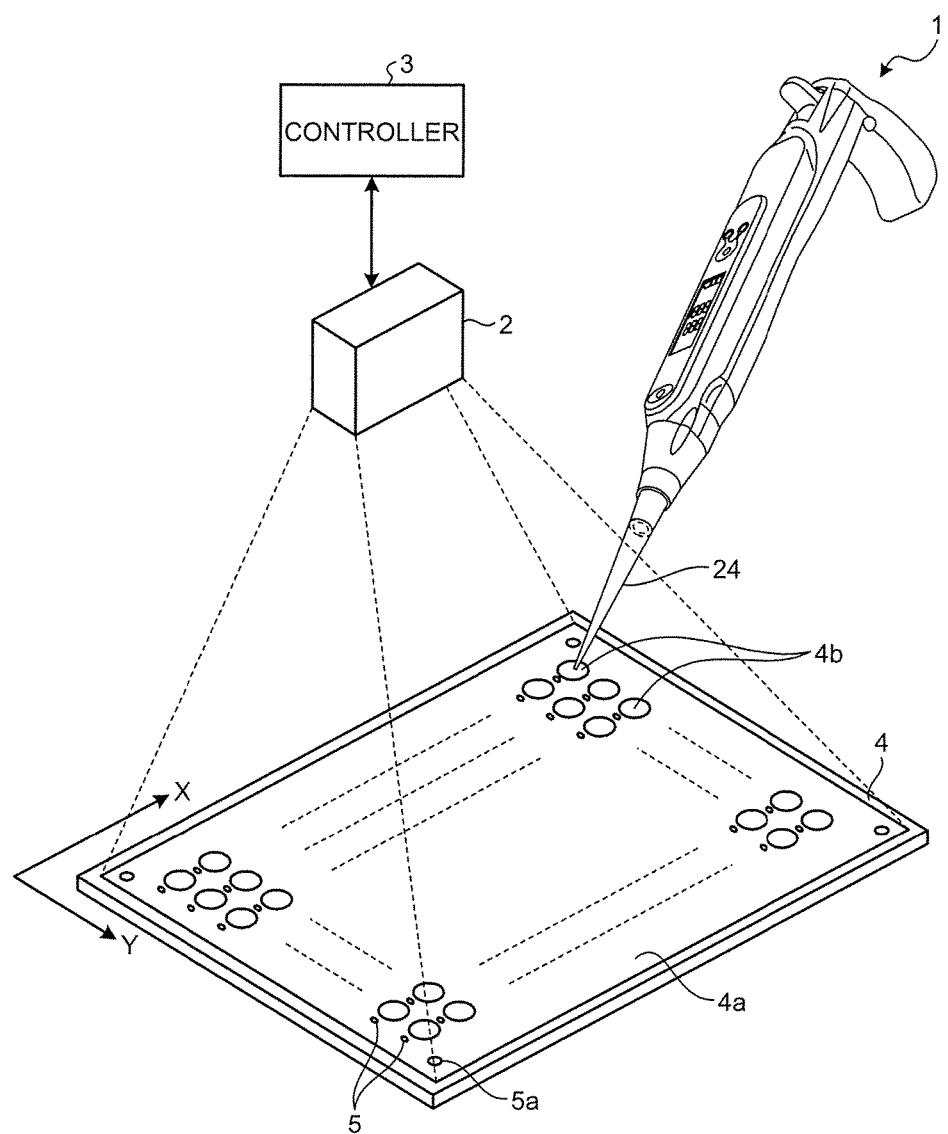
FIG. 4 is an illustration explaining detection of the positional relation between the front-end position of a tip and each well by a positional relation detector.

For example, as illustrated in FIG. 4, a plurality of wells 4b, the number of which is 96, are arranged on a front-surface 4a side of a microplate 4 serving as the pipetting container. Pieces of identification information 5 for identifying the respective wells 4b is displayed in a −X direction corresponding to the respective wells 4b. The positional relation detector 2 captures an image of the entire front surface 4a of the microplate 4 and detects the positional relation between the front-end position of the tip 24 and each of the wells 4b. The positional relation detector 2 then determines whether this positional relation indicates a position that allows pipetting. The position that allows pipetting indicates a situation in which the front-end position of the tip 24 is positioned on the well 4b and within a predetermined distance. Instead of the pieces of identification information 5 provided for the respective wells 4b, pieces of identification information 5a that are provided to the respective four corners of the front surface 4a of the microplate 4 may be used for determining whether the tip 24 is at the position that allows pipetting. In this case, the positions of the respective wells 4b on the front surface 4a of the microplate 4 are known.

The identification information acquiring section 6 is, for example, a bar-code reader and acquires identification information such as an experimenter, a laboratory, temperature and humidity, a pipette (the pipetting device 1), the tip 24, reagent/specimen, and a microplate (pipetting container) to transmit the identification information to the controller 3. The identification information is needed for generation of a pipetting log LD described later. The identification information acquiring section 6 may be connected by USB connection or may be connected by wireless communication.

The external device 100 is connected to the controller 3 through the network N such as the Internet. The external device 100 is, for example, an apparatus provided in a place such as an analysis center. The controller 3 is capable of transmitting the generated pipetting log LD to the external device 100 through the network N.

In the controller 3, a display section 131, an informing section 132, a storage section 133, a communication section 134, a clock 137, and an input section 138 are connected to a control section 130. The control section 130 includes a pipetting pattern generating section 135 and a pipetting managing section 136.

The pipetting pattern generating section 135 generates the pipetting pattern D in which a sequence for pipetting into the pipetting container, pipetting positions, pipetting volumes, and the like are set, and stores the pipetting pattern D in the storage section 133. The input section 138 and the identification information acquiring section 6 are used for setting up the pipetting pattern D on a pipetting pattern format displayed on the display section 131.

Figure 5:
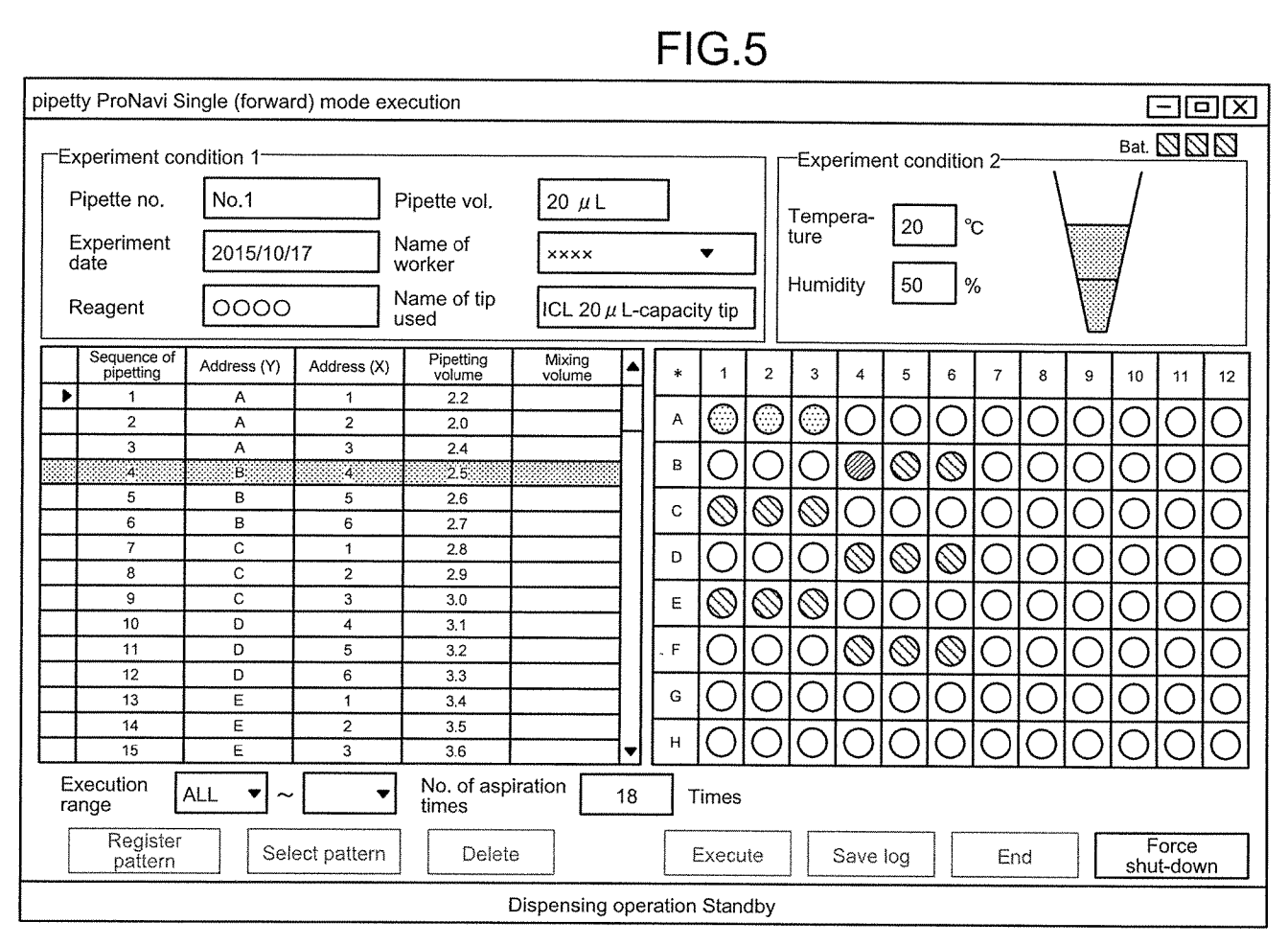

FIG. 5 is a view depicting an example of how the pipetting pattern D is displayed on a display screen. In the pipetting pattern D, the pipetting sequence indicating the sequence for pipetting, the pipetting positions indicating the wells 4b positioned at X-Y positions in the microplate 4, and the pipetting volumes are set as illustrated in FIG. 5. On the display screen, the positions of the respective wells 4b in the microplate 4 are further displayed two-dimensionally as illustrated in the right-hand side of FIG. 5, so that different statuses of pipetting can be displayed in different colors. For example, wells finished with pipetting are displayed in orange color, a well subject to ongoing pipetting is displayed in blue color, and wells on which pipetting is yet to be performed are displayed in green color. For example, when the pipetting device 1 is located at an incorrect pipetting position, this display screen provides assistance for finding out the correct pipetting position. When specific information that needs to be set in the pipetting pattern D is lacking, the control section 130 informs via the informing section 132 that the information is lacking. An experiment date and the like are acquired from the clock 137.

On the display screen, information such as the identification number of the pipetting device 1, the experiment date, the name of reagent, the pipetting capacity of the pipetting device 1, the worker (experimenter), the type of tip, the temperature, the humidity, the remaining pipetting volume, and the remaining battery capacity is displayed.

Pipetting Control Processing by Pipetting Controlling Section

Figure 6:
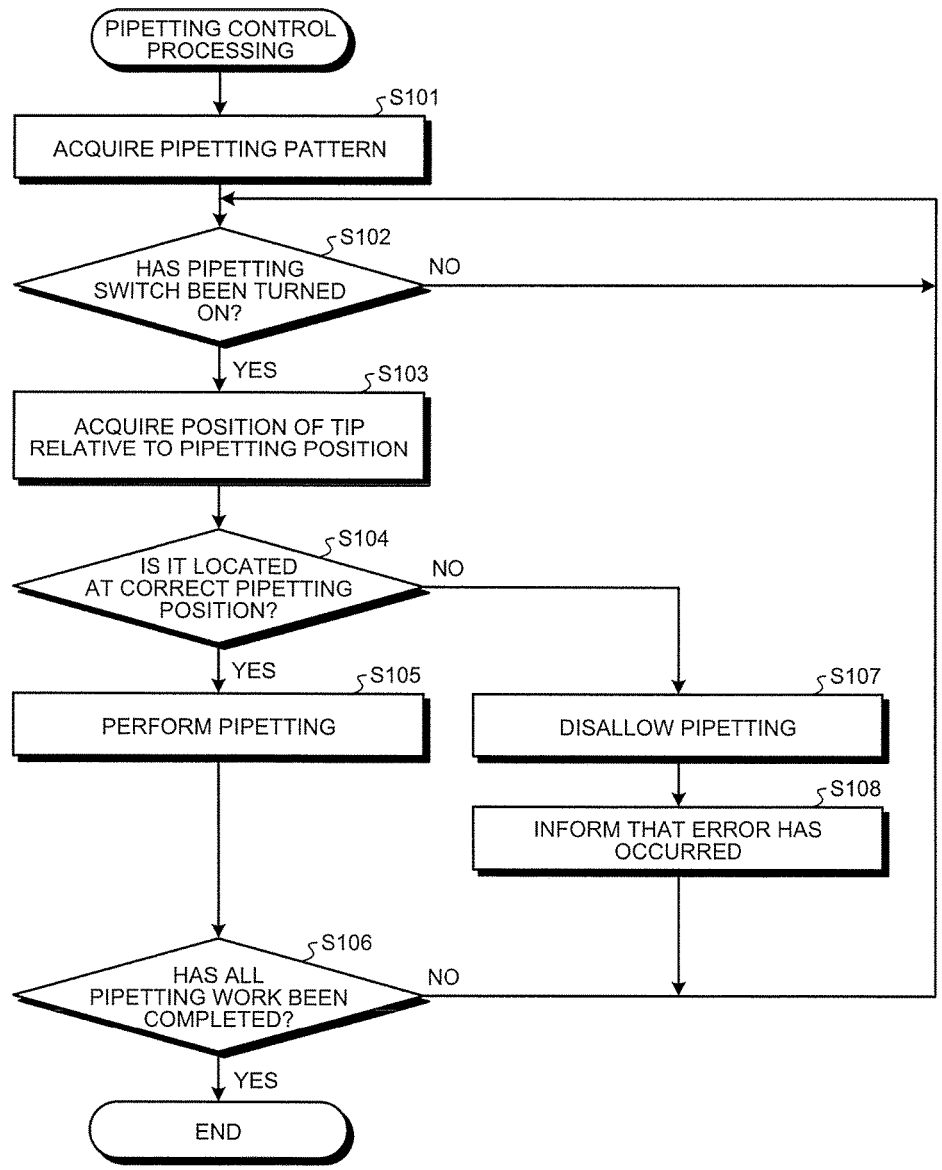
FIG. 6 is a flowchart depicting the procedure of pipetting control processing to be performed by a pipetting controlling section.

Here, the procedure of pipetting control processing to be performed by the pipetting controlling section 81 is described with reference to the flowchart illustrated in FIG. 6. At the start, the pipetting controlling section 81 acquires the pipetting pattern D from the controller 3 (Step S101). The acquired pipetting pattern D is saved as the pipetting pattern D' in the control circuit unit 80. Thereafter, the pipetting controlling section 81 determines whether the pipetting switch SW has been turned on as a result of pushing of the first push button 41 (Step S102). If the pipetting switch SW has been turned on (Yes at Step S102), the pipetting controlling section 81 further acquires, via the controller 3, the position of the tip 24 relative to a pipetting position (Step S103). The position of the tip 24 has been detected by the positional relation detector 2. That is, the pipetting controlling section 81 acquires information on whether the front-end position of the tip 24 is located at the position that allows pipetting into a well. Thereafter, the pipetting controlling section 81 determines whether the front-end position of the tip 24 is located at a correct pipetting position (Step S104). That is, on conditions that the front-end position of the tip 24 is located at the position that allows pipetting into a well and that this well corresponds to a well indicated by the pipetting pattern D', the pipetting controlling section 81 determines that the tip 24 is located at a correct pipetting position.

If the front-end position of the tip 24 is located at a correct pipetting position (Yes at Step S104), the pipetting controlling section 81 allows pipetting and drives the pipetting mechanism 90, thereby executing pipetting (Step S105). Thereafter, with reference to the pipetting pattern D', the pipetting controlling section 81 determines whether all pipetting work has been completed (Step S106). If all pipetting work has been completed (Yes at Step S106), the processing is simply ended. If at least some of the pipetting work has not been completed (No at Step S106), the processing is shifted to Step S102 so that the next pipetting can be performed.

If the front-end position of the tip 24 is not located at a correct pipetting position (No at Step S104), the pipetting controlling section 81 disallows pipetting (Step S107), informs via the informing section 47 that an error has occurred (Step S108), and shifts the processing to Step S102. At the informing, the pipetting controlling section 81 may provide, via the informing section 47, a guide to the correct pipetting position instead of informing that an error has occurred. Obviously, the informing section 47 may be configured to be triggered by the informing of an error to urge that the correct pipetting position is confirmed with reference to the current state of the pipetting pattern D displayed on the display section 131 of the controller 3. Furthermore, it is preferable that the pipetting device 1 notify the controller 3 of information on pipetting execution each time execution of pipetting into one pipetting position is completed, and have the above-described execution statuses of the pipetting pattern displayed on the display section 131 updated.

Incorrectly positioned pipetting can be prevented by performing such pipetting control processing as described above.

Generation of Pipetting Log

The pipetting managing section 136 generates and updates the pipetting log LD based on the pipetting pattern D and the identification information acquired by the identification information acquiring section 6, or information input through the input section 138 and pipetting execution information transmitted as needed from the pipetting device 1, and saves the pipetting log LD in the storage section 133.

FIG. 7 is a view depicting an example of the pipetting log LD. The pipetting log LD illustrated in FIG. 7 has pipetting history generated therein while having therein the information displayed on the display screen that displays the pipetting pattern D illustrated in FIG. 5. The pipetting log LD illustrated in FIG. 7 further has pipetting speeds and pipetting clock times entered as log items.

Generation and saving of the pipetting log LD as described above can increase reproducibility of experiments and prevent fraud in experiments.

According to the disclosure, when a pipetting switch that orders pipetting is turned on, if the front-end position of a tip detected by a positional relation detector is located at a pipetting position indicated by a pipetting pattern set up in advance, a pipetting controlling section allows pipetting corresponding to the pipetting pattern. If the front-end position of the tip detected by the positional relation detector is not located at the pipetting position indicated by the pipetting pattern set up in advance, the pipetting controlling section disallows the pipetting. Incorrectly positioned pipetting can be thus prevented.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A pipetting system comprising:
   a pipetting container including a plurality of wells into which liquid is dispensed;
   a pipetting device including:
      a piston;
      an actuator coupled with the piston to drive the piston;
      a syringe in which the piston is reciprocated in an axial direction of the piston by the actuator;
      a nozzle at a front end of the syringe; and
      a tip attached to the nozzle at the front end of the syringe;
      circuitry configured to control the actuator to drive the piston to aspirate or dispense the liquid through the tip, the circuitry having pipetting pattern data based on which the circuitry controls the actuator to drive the piston to dispense the liquid to the plurality of wells of the pipetting container; and
      a switch configured to activate the circuitry to dispense the liquid to each of the plurality of wells; and
   a detector configured to detect a positional relation between a front-end position of the tip and each of the plurality of wells, wherein the circuitry, activated by the switch, is configured to receive the detected positional relation from the detector to determine whether the front-end position of the tip is located at one of the plurality of wells identified in the pipetting pattern data,
   in response to determining that the front-end position of the tip is located at the one of the wells identified in the pipetting pattern data, the circuitry is configured to control the actuator to drive the piston to dispense the liquid into the one of the plurality of wells based on the pipetting pattern data, and
   in response to determining that the front-end position of the tip is not located at the one of the plurality of wells identified in the pipetting pattern data, the circuitry is configured not to control the actuator to drive the piston,
   the pipetting system further comprises a controller coupled to the pipetting device and the detector, the controller being configured to generate the pipetting pattern data and transmit the pipetting pattern data to the pipetting device,
   the circuitry is configured to notify the controller of information on a current state of dispensing the liquid to the plurality of wells each time when dispersing the liquid to one of the plurality of wells in the pipetting container is completed, and
   the controller includes a display and is configured to receive the information to display the current state of dispensing the liquid to the plurality of wells on the display.

2. The pipetting system according to claim 1, wherein the pipetting pattern data includes at least a sequence for pipetting, positions of the plurality of wells, and pipetting volumes.

3. The pipetting system according to claim 1, wherein the circuitry is further configured to generate an error message in response to determining that the front-end position of the tip is not located at the one of the plurality of wells identified in the pipetting pattern data.

4. The pipetting system according to claim 1, wherein the circuitry is further configured to generate a message specifying that the one of the plurality of wells identified in the pipetting pattern data in response to determining that the front-end position of the tip is not located at the one of the plurality of wells identified in the pipetting pattern data.

5. The pipetting system according to claim 1, wherein the controller is configured to generate a pipetting log based on the information from the circuitry.

* * * * *